(12) United States Patent
Suzuki et al.

(10) Patent No.: US 10,722,112 B2
(45) Date of Patent: Jul. 28, 2020

(54) MEASURING DEVICE AND MEASURING METHOD

(71) Applicant: HAMAMATSU PHOTONICS K.K., Hamamatsu-shi, Shizuoka (JP)

(72) Inventors: Kazutaka Suzuki, Hamamatsu (JP); Yoshinori Matsui, Hamamatsu (JP); Haruyoshi Toyoda, Hamamatsu (JP); Munenori Takumi, Hamamatsu (JP); Naotoshi Hakamata, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/101,169

(22) PCT Filed: Nov. 14, 2014

(86) PCT No.: PCT/JP2014/080238
§ 371 (c)(1),
(2) Date: Jun. 2, 2016

(87) PCT Pub. No.: WO2015/083524
PCT Pub. Date: Jun. 11, 2015

(65) Prior Publication Data
US 2016/0302662 A1 Oct. 20, 2016

(30) Foreign Application Priority Data
Dec. 3, 2013 (JP) .................... 2013-250378

(51) Int. Cl.
*A61B 3/113* (2006.01)
*A61B 3/10* (2006.01)
(Continued)

(52) U.S. Cl.
CPC ............ *A61B 3/113* (2013.01); *A61B 3/0008* (2013.01); *A61B 3/0025* (2013.01); *A61B 3/10* (2013.01);
(Continued)

(58) Field of Classification Search
CPC .......... A61B 3/113; A61B 3/12; A61B 3/102; A61B 3/117; A61B 3/0008; A61B 3/14;
(Continued)

(56) References Cited

U.S. PATENT DOCUMENTS 4,993,825 A * 2/1991 Abe .................. A61B 3/113
351/210
6,542,081 B2 * 4/2003 Torch .................. A61B 3/0066
340/573.1
(Continued)

FOREIGN PATENT DOCUMENTS

CN 1960670 5/2007
CN 101209207 7/2008
(Continued)

OTHER PUBLICATIONS

International Preliminary Report on Patentability dated Jun. 16, 2016 for PCT/JP2014/080238.

*Primary Examiner* — Thomas K Pham
*Assistant Examiner* — Alberto J Betancourt
(74) *Attorney, Agent, or Firm* — Faegre Drinker Biddle & Reath LLP

(57) ABSTRACT

A tablet terminal 1A is a measurement apparatus for measuring a subject's eyelid position, and includes a display section 3 that generates a vertically long light emitting region to make a reflection image form on a corneal surface of the subject's eyeball, a camera 5 that images the reflection image formed by the display section 3, and an arithmetic circuit 7 that derives reflection image information concern-
(Continued)

ing a size or position of the reflection image based on image data of the reflection image obtained by the camera 5, and measures the eyelid position based on the reflection image information.

12 Claims, 15 Drawing Sheets

(51) Int. Cl.
  *A61B 3/00* (2006.01)
  *A61B 3/14* (2006.01)
  *G01B 11/25* (2006.01)
  *G06K 9/00* (2006.01)
  *G06T 7/73* (2017.01)

(52) U.S. Cl.
  CPC ............... *A61B 3/102* (2013.01); *A61B 3/14* (2013.01); *G01B 11/25* (2013.01); *G06K 9/00604* (2013.01); *G06T 7/73* (2017.01); *G06F 2203/011* (2013.01); *G06T 2207/30201* (2013.01)

(58) Field of Classification Search
  CPC ..... A61B 3/1005; A61B 3/1025; A61B 3/112; A61B 5/16; A61B 5/1103; A61B 3/0058; A61B 3/113; A61B 5/1128; G06T 2207/30041; G06F 3/013; G02B 27/0093
  USPC .................................. 351/205, 208–210, 212
  See application file for complete search history.

(56) References Cited

U.S. PATENT DOCUMENTS

| | | | |
|---|---|---|---|
| 7,001,018 B1* | 2/2006 | Martin | A61F 9/008 351/208 |
| 2009/0018419 A1* | 1/2009 | Torch | A61B 3/0066 600/318 |
| 2009/0175613 A1* | 7/2009 | Thorn | G06T 5/005 396/158 |
| 2009/0299209 A1* | 12/2009 | Farbos | A61B 5/1103 600/544 |
| 2010/0245093 A1* | 9/2010 | Kobetski | A61B 5/18 340/576 |
| 2012/0128202 A1* | 5/2012 | Shimizu | H04N 5/23277 382/103 |
| 2012/0293773 A1 | 11/2012 | Publicover et al. | |
| 2013/0050587 A1* | 2/2013 | Namekata | G02F 1/133603 348/739 |
| 2015/0153950 A1* | 6/2015 | Chang | G06F 3/0426 715/773 |

FOREIGN PATENT DOCUMENTS

| | | |
|---|---|---|
| CN | 10126664 | 9/2008 |
| CN | 101264007 | 9/2008 |
| JP | S59-186538 A | 10/1984 |
| JP | H07-313459 A | 12/1995 |
| JP | H11-225966 A | 8/1999 |
| JP | 2000-102510 A | 4/2000 |
| JP | 2000-157493 A | 6/2000 |
| JP | 2007-531579 A | 11/2007 |
| JP | 2008-226047 A | 9/2008 |
| JP | 2009-134276 | 6/2009 |
| JP | 2010-273954 A | 12/2010 |
| WO | WO 2011/050734 | 5/2011 |

* cited by examiner (a) (b)

*Fig.14*
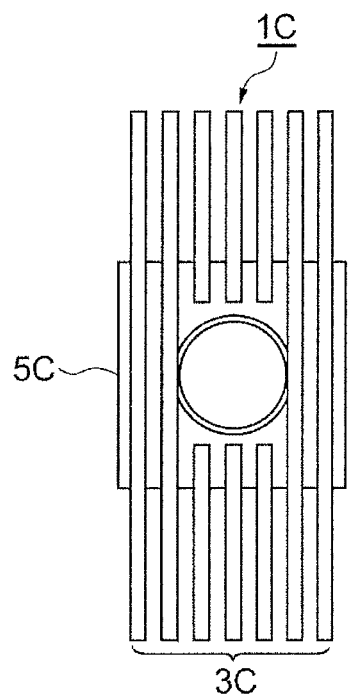
(a)
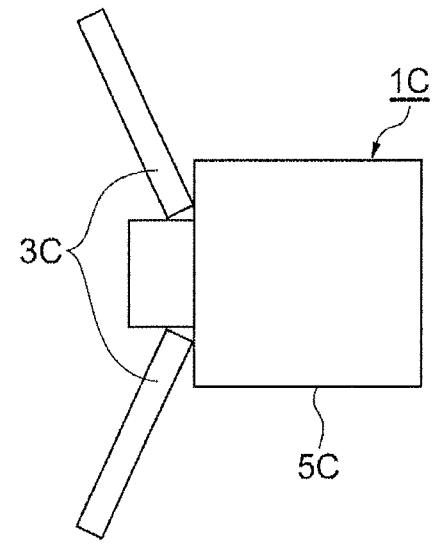
(b)

MEASURING DEVICE AND MEASURING METHOD

TECHNICAL FIELD

The present invention relates to a measurement apparatus and a measurement method for measuring a subject's eyelid position.

BACKGROUND ART

Conventionally, development of measurement methods for the purpose of, for example, diagnosing various diseases by measuring a subject's eye movement has been advanced. For example, with the apparatus described in the following patent document 1, a subject's eye image obtained by a camera is observed as a target for changes in density value in the up-down direction, and an eyelid position is measured by using that the density value changes between the eyelid and eyeball. Also, with the apparatus described in the following patent document 2, a subject moving image is obtained by a camera, and an edge line to serve as a candidate for a combination of the upper and lower eyelids is extracted based on the brightness/darkness of the moving image, and with the apparatus described in the following patent document 3, a one-dimensional image showing a gray scale variation is extracted based on a luminance distribution from a subject's eye image, and a boundary point between the eyelid and eyeball is detected based on the one-dimensional image. These apparatuses all detect an eyelid position by processing a subject's image.

On the other hand, with the apparatus described in the following patent document 4, the intensity of reflected light and scattered light of light that are irradiated a subject's eye with is detected by a sensor to thereby generate a signal indicating whether the eyelid is in an open state or a closed state. This apparatus includes a detection device incorporated with an emitter and a sensor, and discriminates whether the eyelid is in an open state or a closed state by using that return light is weak at the surface of an eye and return light is strong at the surface of an eyelid.

CITATION LIST

Patent Literature

Patent Document 1: Japanese Unexamined Patent Publication No. 2000-102510
Patent Document 2: Japanese Unexamined Patent Publication No. 2008-226047
Patent Document 3: Japanese Unexamined Patent Publication No. H7-313459
Patent Document 4: Japanese Unexamined Patent Publication No. 2007-531579

SUMMARY OF INVENTION

Technical Problem

However, with measurement methods in the apparatuses described in patent documents 1 to 3 described above, when measuring an eyelid position based on a change in luminance value, a precise measurement of the eyelid position has tended to be difficult due to the influence of the generation of scattered light at the eyelid or the influence of eyelashes. Also, with the apparatus described in patent document 4, because scattering conditions of light at the eyelid vary depending on a skin condition and makeup, it is difficult to precisely measure the eyelid position. Also, this apparatus detects a scattered light due to eyelashes and therefore has a lower precision.

Therefore, the present invention has been made in view of such problems, and an object thereof is to provide a measurement apparatus and a measurement method capable of more precisely measuring a subject's eyelid position.

Solution to Problem

In order to solve the above-mentioned problems, a measurement apparatus according to a mode of the present invention is a measurement apparatus for measuring a subject's eyelid position, and includes a light emitter that generates a vertically long light emitting region to make a reflection image form on a corneal surface of the subject's eyeball, an imaging section that images the reflection image formed by the light emitter, and an arithmetic section that derives reflection image information concerning a size or position of the reflection image based on image data of the reflection image obtained by the imaging section, and measures the eyelid position based on the reflection image information.

Or, a measurement method according to another mode of the present invention is a measurement method for measuring a subject's eyelid position, and includes an illuminating step of making a reflection image form on a corneal surface of the subject's eyeball using a light emitter that generates a vertically long light emitting region, an imaging step of imaging the reflection image formed by the illuminating step, and an arithmetic step of deriving reflection image information concerning a size or position of the reflection image based on image data of the reflection image obtained by the imaging step, and measures the eyelid position based on the reflection image information.

By such a measurement apparatus or measurement method, a reflection image is formed on a subject's corneal surface in response to a light emission of the vertically tong light emitting region, and the reflection image is imaged. Then, reflection image information is derived from image data of the obtained reflection image, and an eyelid position is measured from the reflection image information. Thus using a reflection image on the corneal surface improves the detection accuracy of an eyelid position because the image is likely to become relatively bright as compared with when using scattered light in the subject. Also, the influence of eyelashes and the influence of variation in light scattering conditions are unlikely to be received. Consequently, eyelid position detection that is higher in accuracy is enabled with a simple apparatus configuration.

Advantageous Effects of Invention

According to the present invention, a subject's eyelid position can be more precisely detected.

BRIEF DESCRIPTION OF DRAWINGS

FIG. 14 includes views showing an external configuration of a measurement apparatus 1C according to a modification of the present invention.

DESCRIPTION OF EMBODIMENTS

Figure 1:
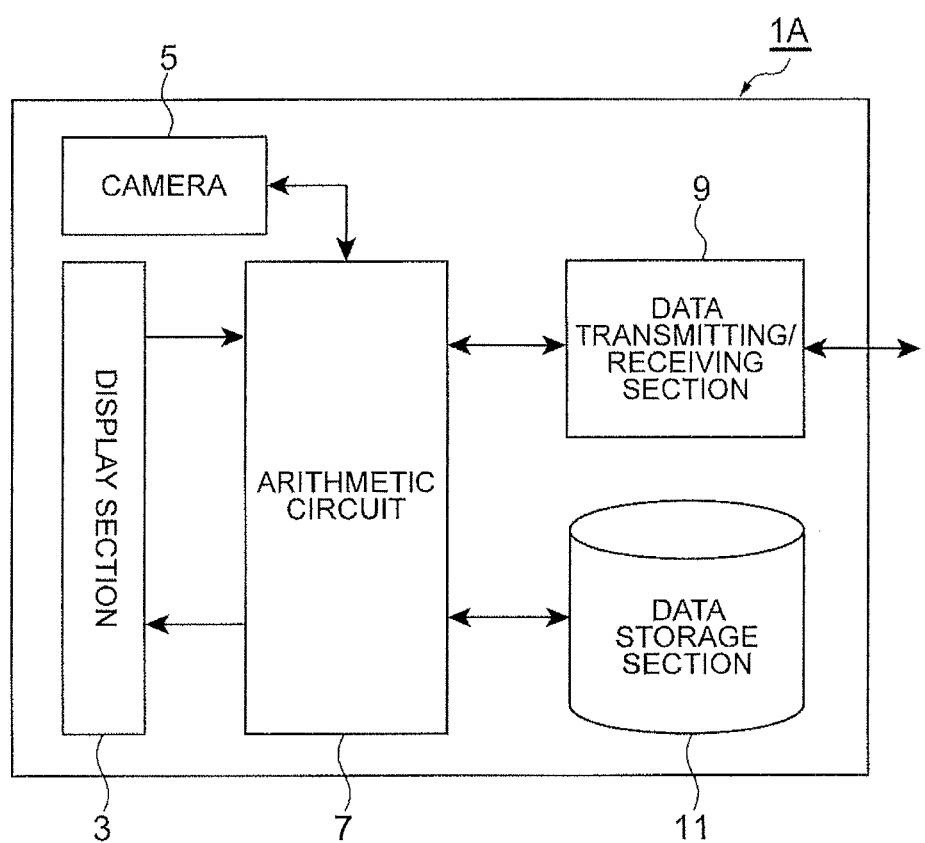
FIG. 1 is a block diagram showing a functional configuration of a tablet terminal 1A which is a measurement apparatus according to a preferred embodiment of the present invention.

Hereinafter, an embodiment of a measurement apparatus and a measurement method according to the present invention will be described in detail with reference to the accompanying drawings. In addition, the same components will be denoted by the same reference signs in the description of the drawings, and overlapping description will be omitted. Also, the respective drawings are prepared for the purpose of description, and are drawn so that the portions to be described are especially emphasized. Therefore, the dimensional ratios of the respective members in the drawings are not always coincident with actual ratios.

Figure 2:
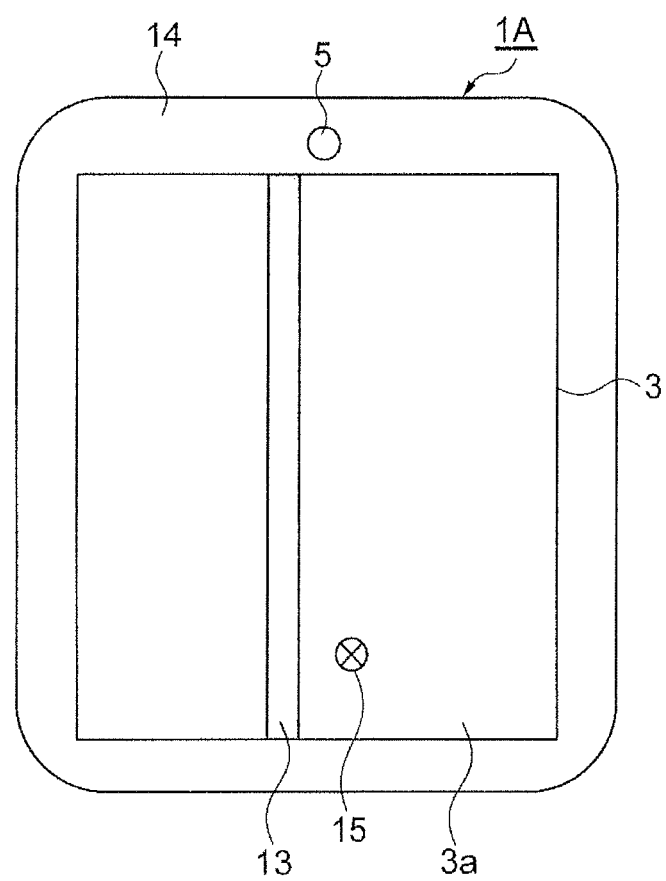
FIG. 2 is a plan view showing an external appearance of the tablet terminal 1A in FIG. 1.

FIG. 1 is a block diagram showing a functional configuration of a tablet terminal 1A which is a measurement apparatus according to a preferred embodiment of the present invention, and FIG. 2 is a plan view showing an external appearance of the tablet terminal 1A. This tablet terminal 1A is an information processing terminal capable of measuring a subject's eyelid position, and is constructed including a display section 3 that serves as a light emitter, a camera (imaging section) 5 incorporated with an image sensor, an arithmetic circuit (arithmetic section) 7, a data transmitting/receiving section 9 that transmits and receives data (to be) processed by the arithmetic circuit 7 with the outside, and a data storage section 11 that stores data (to be) processed by the arithmetic circuit 7.

The display section 3 is a so-called touch panel display device, and is a display device on a screen 3a of which disposed in the center of an outer surface of a housing 14 of the tablet terminal 1A a screen operation by a user's finger is enabled and which is also capable of displaying data, an image, etc., on the screen 3a. The display section 3 hands over data or an instruction signal input by the screen operation to the arithmetic circuit 7, and also receives from the arithmetic circuit 7 character data, numerical data, and image data as display target. Also, the display section 3, when a subject's eyelid position measurement is being executed, causes an image as shown in FIG. 2 to be displayed on the screen 3a based on the data received from the arithmetic circuit 7. That is, the display section 3 generates a vertically long band-like high-luminance light emitting region 13 in a center of the screen, and also causes a marker (indicator) 15 for adjusting the subject's gazing point during measurement to be displayed. This causes a high-luminance scattered light to be irradiated from the light emitting region 13 at the time of eyelid position measurement.

The camera 5 is an imaging device incorporated with an image sensor such as a CMOS or CCD and an optical element for forming an image on the image sensor, is disposed outside of the screen 3a on the surface of the housing 14, and is set such that its imaging optical axis is directed outside substantially perpendicularly from the surface of the housing 14. The camera 5 images a subject's eye to successively obtain eye images at the time of eyelid position measurement. The camera 5 is controlled in its operation by the arithmetic circuit 7, and also outputs image data concerning the obtained eye image to the arithmetic circuit 7.

The arithmetic circuit 7 is a circuit section that arithmetically processes various types of data, and at the time of eyelid position measurement performs an arithmetic operation (hereinafter, referred to as an "eyelid position measurement processing") for image data obtained by the camera 5 as a target and generates a measurement result. Concretely, the arithmetic circuit 7 specifies a reflection image formed on a corneal surface of the subject's eyeball based on the image data, and derives reflection image information concerning a size or position on an eye image of the reflection image. Further, the arithmetic circuit 7 measures an eyelid position based on the derived reflection image information, calculates a blink feature amount by analyzing the eyelid position in time series, and then obtains a measurement result corresponding to the blink feature amount. Also, the arithmetic circuit 7 is enabled to cause the display section 3 to display a generated measurement result, or is enabled as well to transmit the same to the outside such as the Internet via the data transmitting/receiving section 9.

The data transmitting/receiving section 9 transmits data such as the measurement result generated by the arithmetic circuit 7 to the outside such as the Internet by using wireless communication such as mobile communication or wireless LAN communication. Also, the data transmitting/receiving section 9 is enabled as well to receive data such as a diagnostic result on a measurement result from the outside by wireless communication and hand over the data to the arithmetic circuit 7. The data storage section 11 is a memory (storage device) that stores data to be referenced to in arithmetic processing by the arithmetic circuit 7 and data generated by said arithmetic processing.

Next, arrangement conditions for imaging a reflection image on a subject's corneal surface in the tablet terminal 1A will be described.

Figure 3:
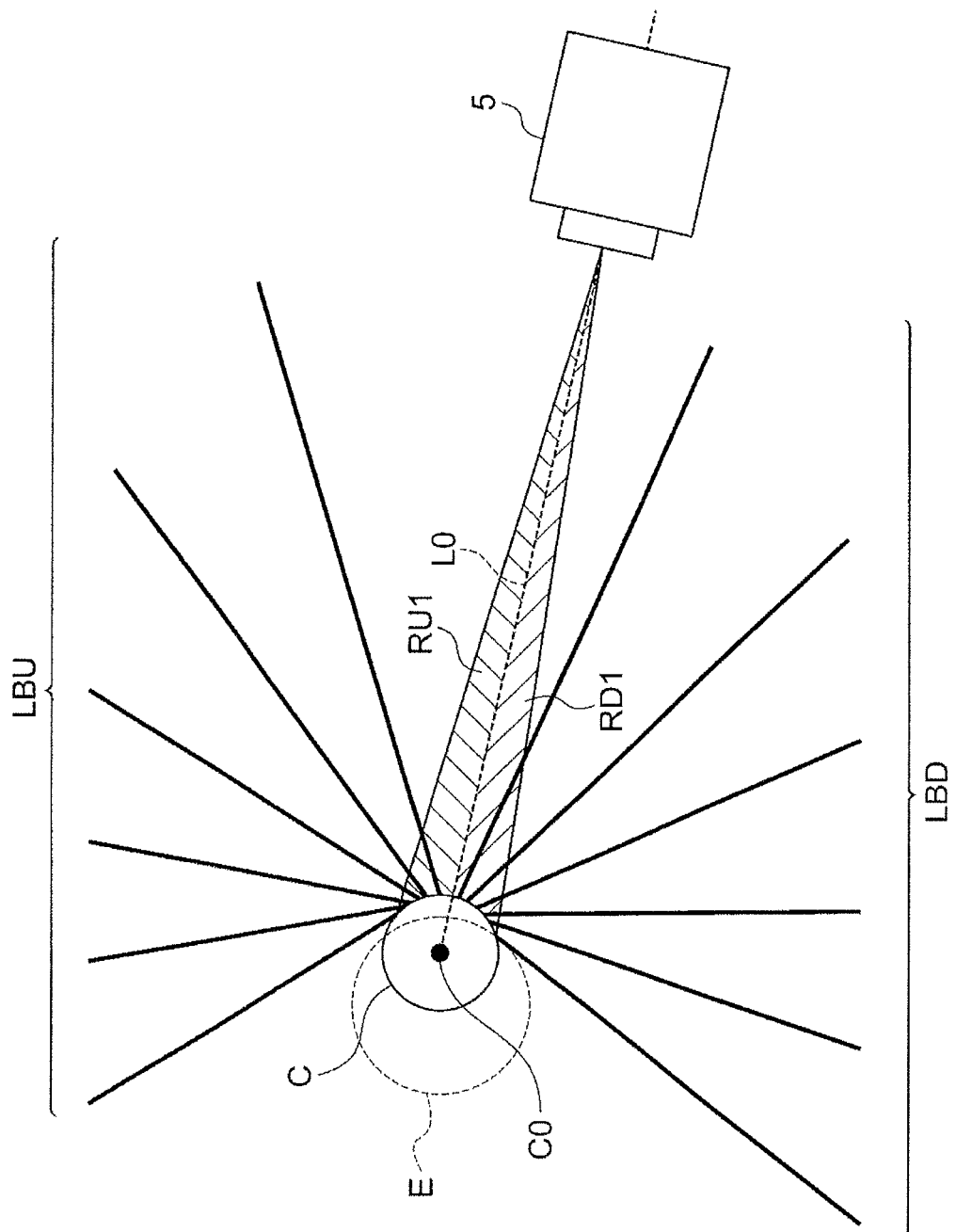
FIG. 3 is a side view showing a reflection state of scattered light to the camera 5 in response to various incident angles on a subject's eye of scattered light irradiated from the display section 3 in FIG. 1.

FIG. 3 is a side view, viewed from a subject's lateral side, of a reflection state of scattered light to the camera 5 in response to various incident angles on the subject's eye of scattered light irradiated from the display section 3. As shown in the same figure, at the time of eyelid position measurement, the imaging optical axis of the camera 5 is set so as to approximate a line L0 connecting the camera 5 and a central point C0 of a cornea C of a subject's eyeball E. When assuming a case where scattered lights LBU are irradiated at that time from a side over the subject's eyeball E, a reflection image formed on the surface of the cornea C by those scattered lights LBU forms an image on the camera 5 by way of a route RU1 higher than the line L0. Therefore, a reflection image of the scattered lights LBU that is imaged by the camera 5 appears at an upper side of the eyeball in the subject's eye image. On the other hand, when assuming a case where scattered lights LBD are irradiated from a side under the subject's eyeball E, a reflection image formed on the surface of the cornea C by those scattered lights LBD form an image on the camera 5 by way of a route RD1 lower than the line L0. Therefore, a reflection image of the scattered lights LBD that is imaged by the camera 5 appears at a lower side of the eyeball in the subject's eye image.

Figure 4:
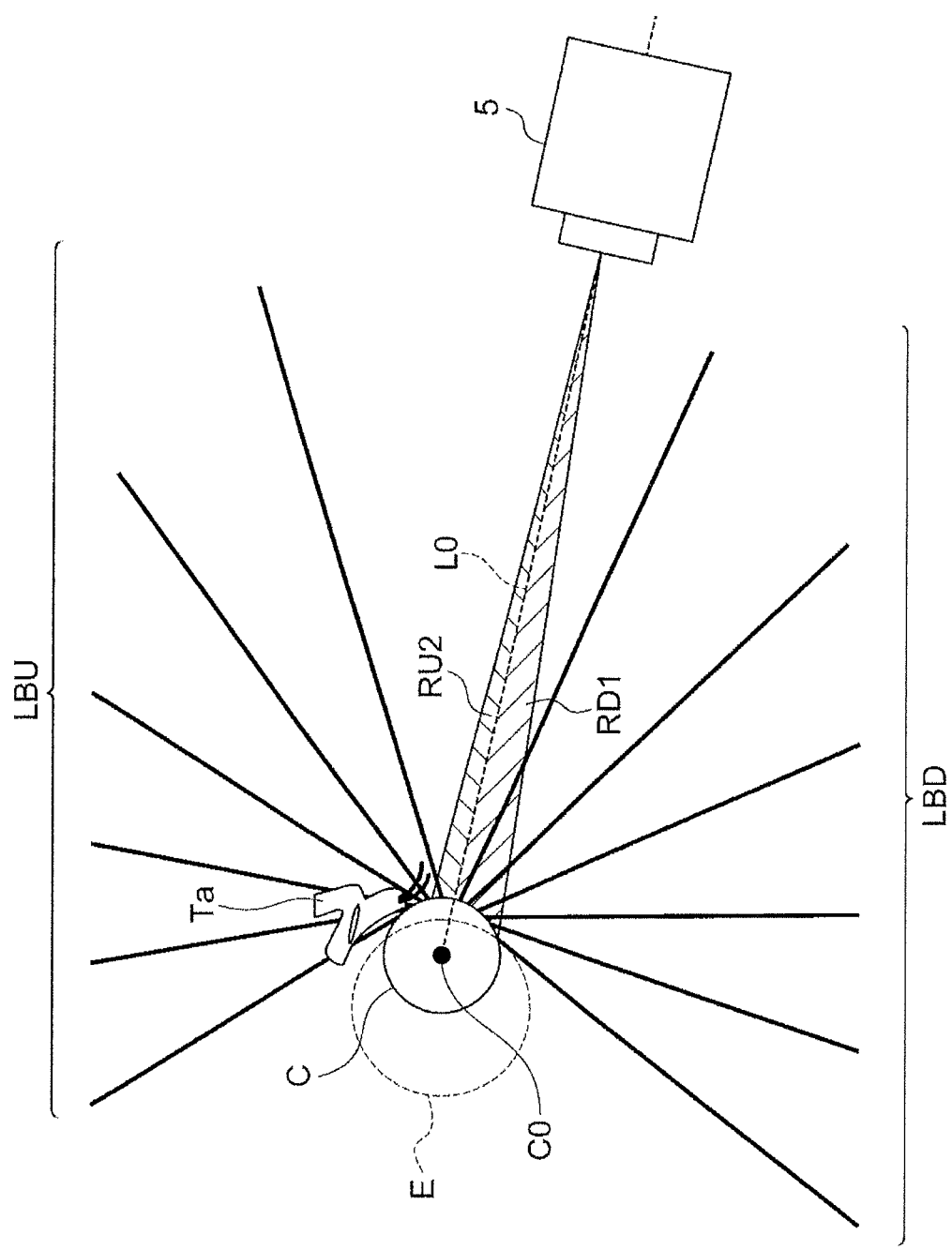
FIG. 4 is a side view showing a reflection state of scattered light to the camera 5 in response to various incident angles on a subject's eye of scattered light irradiated from the display section 3 when the degree of closing of the subject's eyelid is small.
Figure 5:
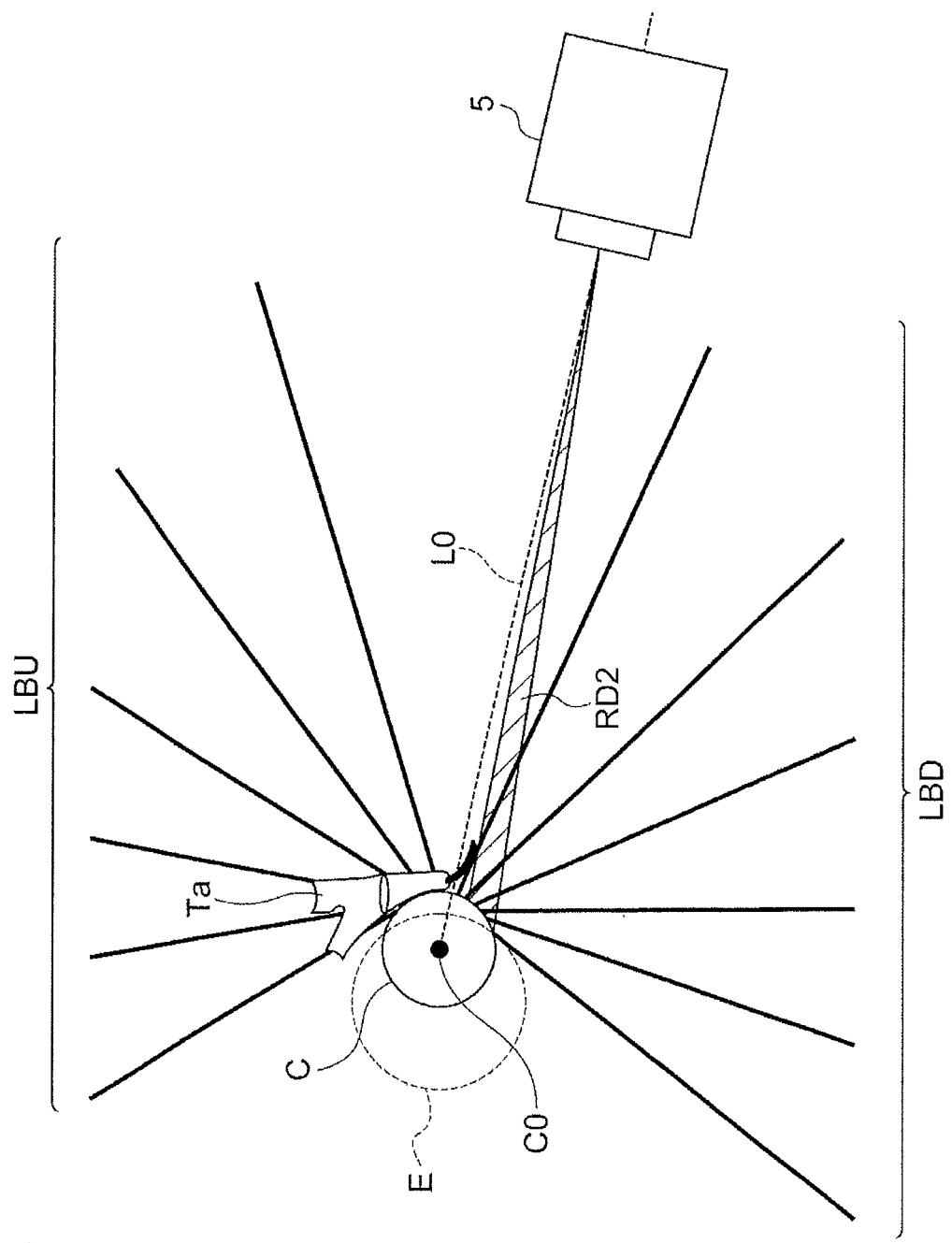
FIG. 5 is a side view showing a reflection state of scattered light to the camera 5 in response to various incident angles on a subject's eye of scattered light irradiated from the display section 3 when the degree of closing of the subject's eyelid is great.

FIG. 4 is a side view showing a reflection state of scattered light to the camera 5 in response to various incident angles on the subject's eye of scattered light when the degree of closing of the subject's eyelid is small, and FIG. 5 is a side view showing a reflection state of scattered light to the camera 5 in response to various incident angles on the subject's eye of scattered light when the degree of closing of the subject's eyelid is great. As shown in FIG. 4, when the subject's eyelid is slightly closed, an upper side of a route RU2 of reflected light of scattered lights LBU is blocked, so that a reflection image of the scattered lights LBU to be imaged by the camera 5 wanes at its upper side by a length corresponding to the eyelid position. On the other hand, as shown in FIG. 5, when the subject's eyelid is largely closed, reflected light of the scattered lights LBU is entirely blocked not to be detected by the camera 5. At this time, an upper side of a route RD2 of reflected light of scattered lights LBD is blocked, so that a reflection image of the scattered lights LBD to be imaged by the camera 5 wanes at its upper side by a length corresponding to the eyelid position.

In consideration of the reflection states of the scattered lights LBU and LBD mentioned above, at the time of eyelid position detection by the tablet terminal 1A, an arrangement state of the tablet terminal 1A with respect to the subject is set as follows in order to accurately measure an eyelid position. That is, when it is detected in advance that the subject's upper eyelid is present higher than a pupil center, it is set so that scattered lights from the display section 3 are irradiated from an higher side than the subject's front direction. On the other hand, when it is detected in advance that the subject's upper eyelid is present lower than a pupil center, it is set so that scattered lights from the display section 3 are irradiated from a lower side than the subject's front direction. This allows changing the size and shape of a reflection image on the subject's corneal surface to be formed on the camera 5 correspondingly to the eyelid position.

Figure 6:
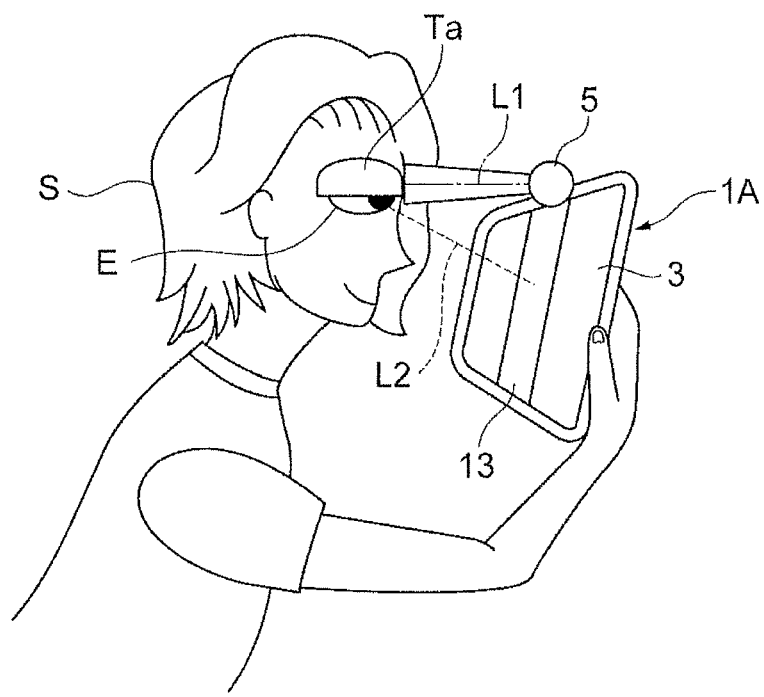
FIG. 6 is a conceptual view showing an arrangement state of the tablet terminal 1A in FIG. 1 with respect to a subject S to be controlled by the tablet terminal 1A.
Figure 7:
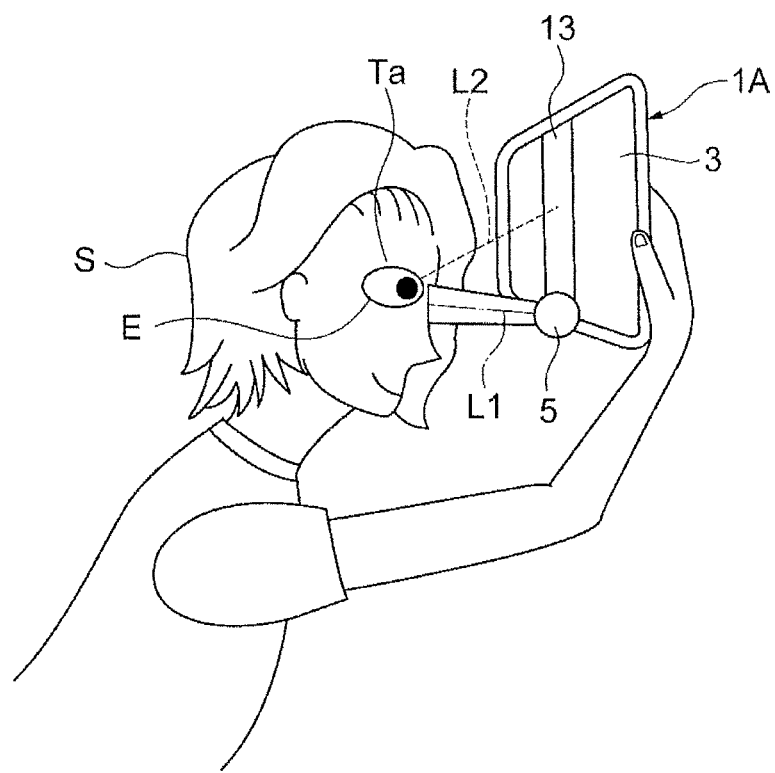
FIG. 7 is a conceptual view showing an arrangement state of the tablet terminal 1A in FIG. 1 with respect to a subject S to be controlled by the tablet terminal 1A.

Such control of the arrangement state of the tablet terminal 1A will be concretely described. FIG. 6 and FIG. 7 are conceptual views showing arrangement states of the tablet terminal 1A with respect to a subject S to be controlled by the tablet terminal 1A. As shown in FIG. 6, when it is detected from image data obtained by the camera 5 that the position of an upper eyelid Ta of the subject S is lower than the pupil center, the way of holding the tablet terminal 1A is controlled by an instruction from the tablet terminal 1A so as to dispose the camera 5 at an upper side and dispose the display section 3 at a lower side as viewed from the subject S. In detail, the control is performed so that an imaging optical axis L1 of the camera is obliquely directed on the corneal surface of an eyeball E with respect to an axis L2 connecting a center of the light emitting region 13 generated by the display section 3 and the eyeball E and scattered lights from the light emitting region 13 are irradiated from a lower side with respect to the front direction of the subject S. On the other hand, as shown in FIG. 7, when it is detected from image data obtained by the camera 5 that the position of an upper eyelid Ta of the subject S is higher than the pupil center, the way of holding the tablet terminal 1A is controlled by an instruction from the tablet terminal 1A so as to dispose the camera 5 at a lower side and dispose the display section 3 at an upper side as viewed from the subject S. In detail, the control is performed so that an imaging optical axis L1 of the camera is obliquely directed on the corneal surface of an eyeball E with respect to an axis L2 connecting a center of the light emitting region 13 generated by the display section 3 and the eyeball E and scattered lights from the light emitting region 13 are irradiated from an upper side with respect to the front direction of the subject S.

Figure 8:
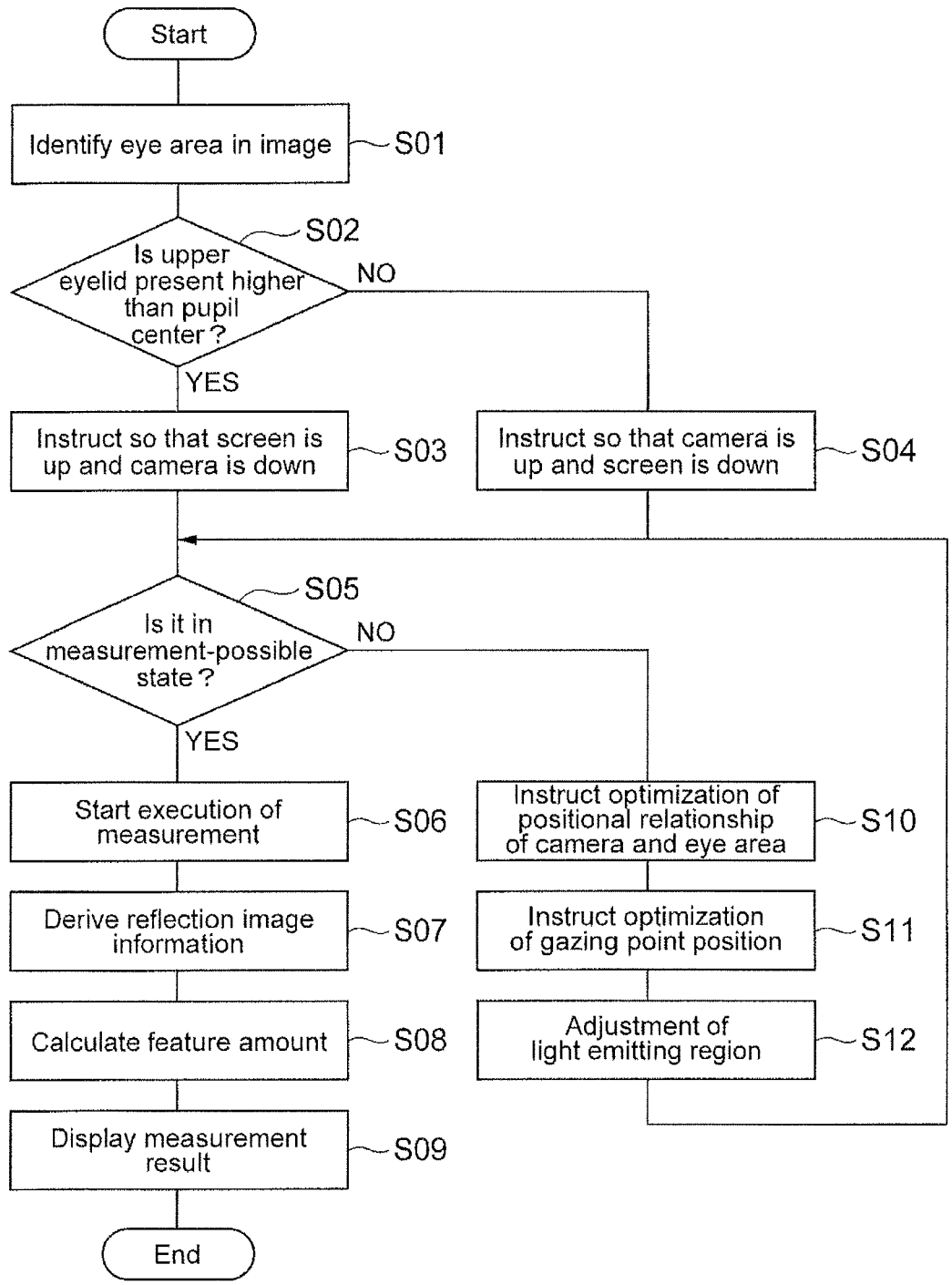
FIG. 8 is a flowchart showing an operating procedure of an eyelid position measurement processing by the tablet terminal 1A in FIG. 1.

In the following, description will be given of an operating procedure of the eyelid position measurement processing by the tablet terminal 1A described above, while the measurement method of the present embodiment will be described in detail. FIG. 8 is a flowchart showing the operating procedure of the eyelid position measurement processing by the tablet terminal 1A.

First, with the tablet terminal 1A being held by a subject in a manner that the camera 5 is located in front of his/her eye area, image data of and around the eye is obtained by the camera 5 with a predetermined operation as a trigger, and subsequently, the eye area is identified in the image data by the arithmetic circuit 7 and the image data of the eye area is extracted therefrom (step S01). As a method for identifying the eye area, a method can be mentioned of making illumination light flicker at a constant period by the display section 3 and identifying sites in image data obtained in time series according thereto that brighten in luminance in synchronization. At that time, identifying sites having luminance equal to or more than a predetermined threshold, setting a region size and then performing a search for the eye area makes it possible to improve search speed. Or, the eye area identification by the arithmetic circuit 7 may be performed by image processing. That is, by the arithmetic circuit 7, an eye area region between an eyebrow part and a nose or mouth part is identified for the subject's color image obtained by the camera 5 as a target. At that time, the eyebrow part is detected as a part extending long sideways where R, G, and B are all dark in luminance and the mouth part is detected as a part having a constant area where R is brighter in luminance than G and B. Also, binarization processing, edge extraction processing, and the like may be applied, by the arithmetic circuit 7, to the subject's monochrome image as a target, followed by matching to face feature information to thereby extract the eye area.

Next, by the arithmetic circuit 7, the position of an upper eyelid and pupil is detected for image data including the extracted eye area as a target, and whether the upper eyelid is present at a side higher than the pupil center is determined (step S02). This determination allows obtaining features of the subject's ordinary eyelid position. At this time, the position of the upper eyelid is detected using a feature that the upper eyelid has a luminance brighter than that of the eye area. Also, in the determination to be performed here, a rate of the area of the upper eyelid covering the eyeball surface to the area of the eyeball may be determined. The distinction between the eyelid and eye area may be performed based on the luminance as above, or may be performed by image processing such as Hough transform or edge extraction. When it is determined as a result of the determination that the upper eyelid is present at a side higher than the pupil center (step S02; YES), it is instructed to the subject by the arithmetic circuit 7 to hold the tablet terminal with the display section 3 up and the camera 5 down (so as to reach the arrangement state shown in FIG. 7) (step S03). On the other hand, when it is determined that the upper eyelid is present at a side lower than the pupil center (step S02; NO), it is instructed to the subject by the arithmetic circuit 7 to hold the tablet terminal with the camera 5 up and the display section 3 down (so as to reach the arrangement state shown in FIG. 6) (step S04). Such an instruction is performed by a display output using the display section 3 or an audio output using a speaker. In addition, the arithmetic circuit 7 may perform a light emission to generate corneal reflected light and may judge that the eyelid is in an open (up) state if corneal reflected light is as a result generated and if not, determine that the eyelid is in a closed (down) state.

Thereafter, by the arithmetic circuit 7, an emission of scattered light from the light emitting region 13 by the display section 3 is started and imaging of the subject's eye area by the camera 5 is also started, and it is determined whether image data obtained by the camera 5 is in a state where an eyelid position measurement is possible (step S05). Here, it is determined if the obtained subject's image is in focus, if a reflection image of scattered light in the eye image is at a measurable position (if a reflection image of scattered light in the eye image is not excessively close to a corner and is at a position that enables a continuous measurement), or the like. When it is determined as a result of the determination that the image data is not in a measurement-possible state (step S05; NO), it is instructed by the arithmetic circuit 7 to optimize the distance and positional relationship of the subject and the camera 5 in order to adjust the image focus and the imaging axis (step S10). Further, by the arithmetic circuit 7, the position of the marker 15 on the screen 3a of the display section 3 is changed, and it is instructed to the subject to change the gazing point to such a position so as to optimize the position of a reflection image in an eye image (step S11). The instruction in step S10, S11 may be performed by a display output using the display section 3 or may be performed by an audio output using a speaker. Next, the light emitting region 13 in the display section 3 is adjusted in luminance and shape in order to enable a stable measurement of a reflection image in an eye image (step S12). For stabilizing the eyelid position detection from reflected light on average, it is preferable to make the shape of the light emitting region 13 thick and vertically long and make the luminance thereof bright, but there is no limitation thereto depending on the subject's eyeball state (for example, when an ocular lens is inserted by surgery). The light emitting region 13 is therefore changed in thickness, luminance, and shape so that a stable measurement becomes possible. At that time, the light emitting region 13 is adjusted based on a variation range of the position or luminance of the reflection image within an arbitrary set period in order to secure a stable measurement. Also, at the time of shape adjustment, the light emitting region 13 may be changed in shape while referencing the shape of the reflection image in real time, or the shape of the light emitting region 13 may be changed to a preset shape. Thereafter, the process is returned to step S05.

Figure 9:
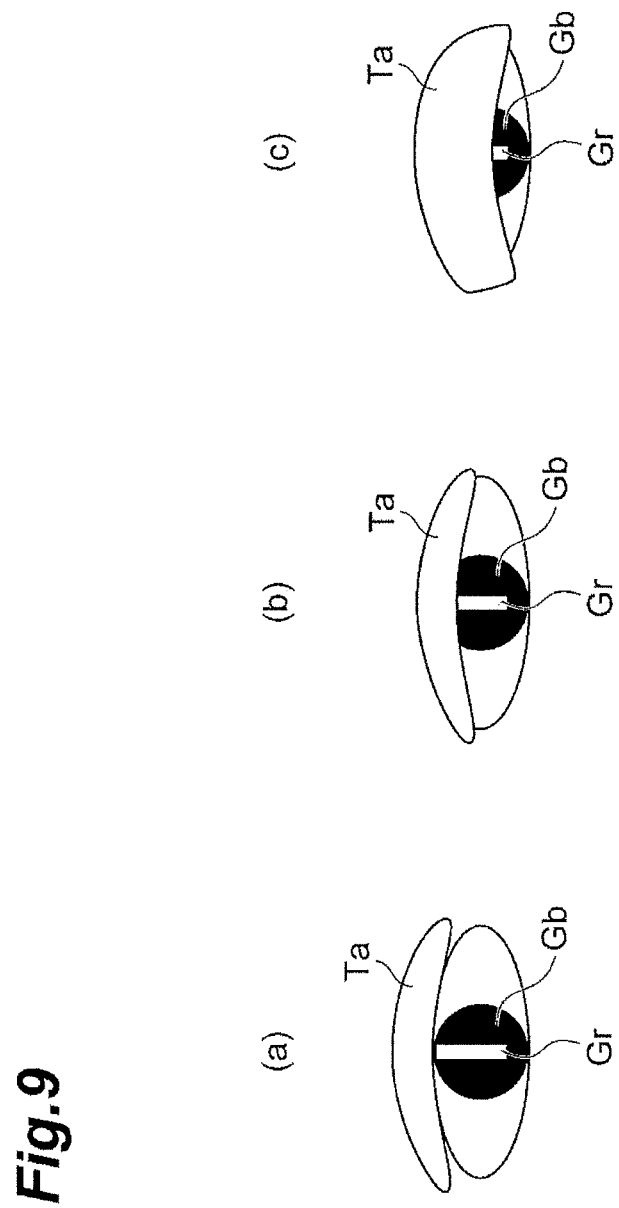
FIG. 9 includes views each showing an example of a subject's eye image to be processed by the arithmetic circuit 7 in FIG. 1.

On the other hand, when it is determined as a result of the determination in step S05 that the image data is in a measurement-possible state (step S05; YES), an eyelid position measurement processing is started for the image data as a target by the arithmetic circuit 7 (step S06). That is, a reflection image formed on a corneal surface of the subject's eyeball is specified based on the image data, and reflection image information of the reflection image concerning a size or position on the eye image is derived (step S07). FIG. 9 shows examples of a subject's eye image to be processed by the arithmetic circuit 7. The portion (a) in FIG. 9 shows an example of a reflection image Gr that is obtained in a state where the subject's upper eyelid Ta is open, the portion (b) in FIG. 9 shows an example of a reflection image Gr that is obtained in a state where the subject's upper eyelid Ta is slightly closed, and the portion (c) in FIG. 9 shows an example of a reflection image Gr that is obtained in a state where the subject's upper eyelid Ta is largely closed. A vertically long, substantially rectangular reflection image Gr is thus formed inside an iris image Gb in the eye image, the waning degree at an upper end of the reflection image Gr corresponds to a closing degree of the upper eyelid.

In order to measure an eyelid position using such properties, the arithmetic circuit 7 derives reflection image information. Examples of such reflection image information that can be mentioned include the area, the overall light amount (emission intensity), the longitudinal length, the length ratio of the right and left sides, the length ratio of the upper and lower bases, the aspect ratio, the longitudinal length ratio with elapse of time (a change in longitudinal length), barycentric coordinates (feature point), or an average of vertex coordinates (feature point). Also, the arithmetic circuit 7 may obtain, as reflection image information, the above-mentioned value when the reflection image Gr is subjected to trapezoidal approximation or a difference between an approximate value of the above-mentioned value when subjected to trapezoidal approximation and an actual measurement value of the above-mentioned value. Further, the arithmetic circuit 7 may obtain, as reflection image information, barycentric coordinates when the reflection image Gr is subjected to elliptical approximation, the length ratio of the long and short sides when the reflection image Gr is subjected to elliptical approximation, or a difference between an approximate value of the area when the reflection image Gr is subjected to elliptical approximation and an actual measurement value of the area.

Figure 10:
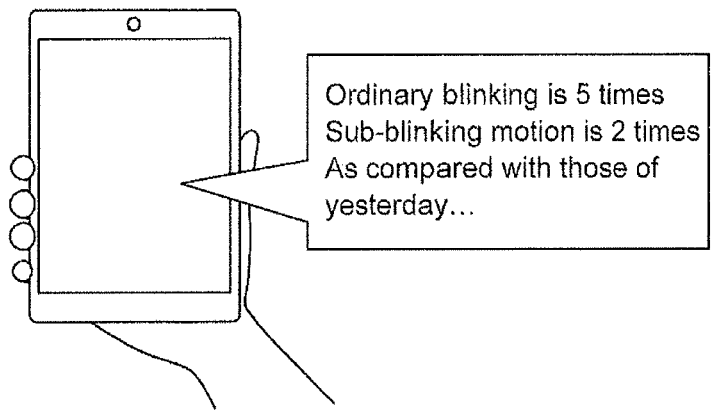
FIG. 10 is a view showing an example of a measurement result displayed on the display section 3 in FIG. 1.
Figure 11:
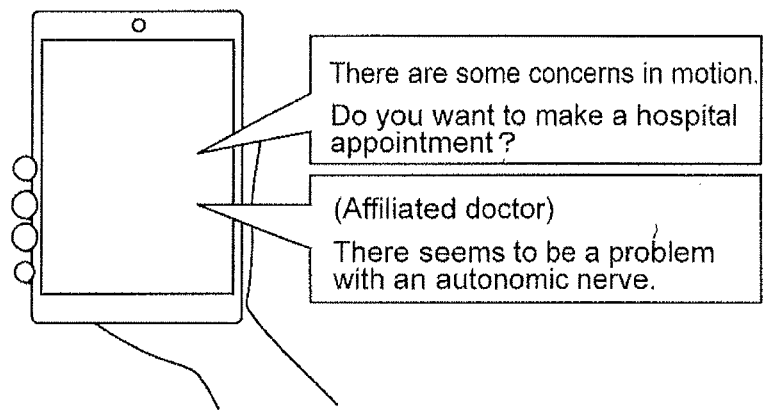
FIG. 11 is a view showing an example of a measurement result and externally received information displayed on the display section 3 in FIG. 1.

Next, the arithmetic circuit 7 measures an eyelid position based on the derived reflection image information, and analyzes the eyelid position for image data obtained in time series as a target to thereby calculate a blink feature amount (step S08). Thereafter, the arithmetic circuit 7 references a database stored in the data storage section 11 based on the blink feature amount, obtains a measurement result corresponding to blinking, and causes the display section 3 to display the measurement result (step S09). FIG. 10 shows an example of the measurement result displayed on the display section 3. Also, the arithmetic circuit 7 may transmit the measurement result to the outside via the data transmitting/receiving section 9 and cause the display section 3 to display externally received information received in response thereto from the outside. FIG. 11 shows an example of the measurement result and externally received information displayed on the display section 3. In addition, as the blink feature amount, a summary value such as a mean, a median, or a standard deviation of calculated values of any of the following can be used.

Eyelid movement distance
Maximum speed during movement
Movement period
Blinking motion interval Or, the number of times of blinking sorted out by any of the following conditions can also be used as the blink feature amount.

Blinking of displacement shorter than eyelid movement distance threshold at blinking
Blinking slower than eyelid movement speed threshold at blinking
Blinking performed in a shorter period than period threshold at blinking By the tablet terminal 1A and the eyelid position measurement method using the same having been described above, a reflection image is formed on a subject's corneal surface in response to a light emission of the vertically long light emitting region 13, and the reflection image is imaged. Then, reflection image information is derived from image data of the obtained reflection image, and an eyelid position is measured from the reflection image information. Thus using a reflection image on the corneal surface that is substantially a spherical surface improves the detection accuracy of an eyelid position because the image is likely to become relatively bright as compared with when using scattered light in the subject. As a result of using reflected light brighter than scattered light, for example, the brightness of reflected light becomes brighter than that of the periphery including other eye area parts at the time of an indoor measurement, which leads to stabilization of an eyelid position measurement. Also, the influence of eyeliner and glitter makeup, the influence of transverse wrinkling of the skin, the influence of eyelashes, and the influence of variation in light scattering conditions due to an ocular lens or the like are unlikely to be received. Consequently, eyelid position detection that is higher in accuracy is enabled with a simple apparatus configuration.

Also, the tablet terminal 1A has the light emitting region 13 that is a band-like planar light emitter generated on the display section 3. Thus using a surface light source allows changing the size and shape of a reflection image to be formed on the subject's corneal surface correspondingly to the eyelid position, which enables determining an eyelid position at a high accuracy with a simple configuration. On the other hand, use of a point light source results only in formation of a light spot on the corneal surface, only blinking of a swing amplitude to shade the light spot can be measured, and not only can detecting blinking motions not be changed in an adaptive manner, but a precise measurement is also hindered if the light spot is shaded by eyelashes.

Also, in the eyelid position measurement processing, because the arithmetic circuit 7 derives reflection image information, the rate of a part that is hidden by the eyelid of the reflection image on the corneal surface is made evaluable, and an eyelid position can be precisely measured by a simple evaluation method. Also, the arithmetic circuit 7 can also use the coordinates of a feature point such as barycentric coordinates or vertex coordinates of the reflection image as reflection image information. Also in this case, the rate of a part that is hidden by the eyelid of the reflection image on the corneal surface is made evaluable, and an eyelid position can be precisely measured by a simple evaluation method.

Further, through control by the tablet terminal 1A, the subject's way of holding the tablet terminal 1A can be led to an optimal way. That is, the optical axis of the camera 5 is set so as to be obliquely directed on the corneal surface with respect to an axis connecting the light emitting region 13 and the eyeball, and also, an irradiation direction of scattered light from the light emitting region 13 onto the subject is set according to the subject's ordinary eyelid position. In this manner, the reflection image on the corneal surface can be reliably captured by the camera 5. Also, an eyelid position measurement is enabled by the subject alone without the necessity of assistance from a measurement assistant or the like.

Also, by the arithmetic circuit 7, the subject's gaze is guided so as to optimize the position of a reflection image in the eye image. The upper eyelid position with respect to an axis connecting the camera 5 and a center of the subject's eye area can thereby be guided to an optimal position, and an eyelid position with respect to the eye area can be more precisely measured.

However, the present invention is not limited to the embodiment described above. For example, a desktop type or notebook type of computer terminal or another information processing terminal having a camera and a data communication function such as a portable telephone or smartphone may be adopted in place of the tablet terminal 1A. Also, the arithmetic function realized in the present embodiment may be realized by software, or may be realized by hardware such as an arithmetic circuit. Examples of the realization by hardware include use of an intelligent vision sensor (IVS) manufactured by Hamamatsu Photonics K.K.

Figure 12:
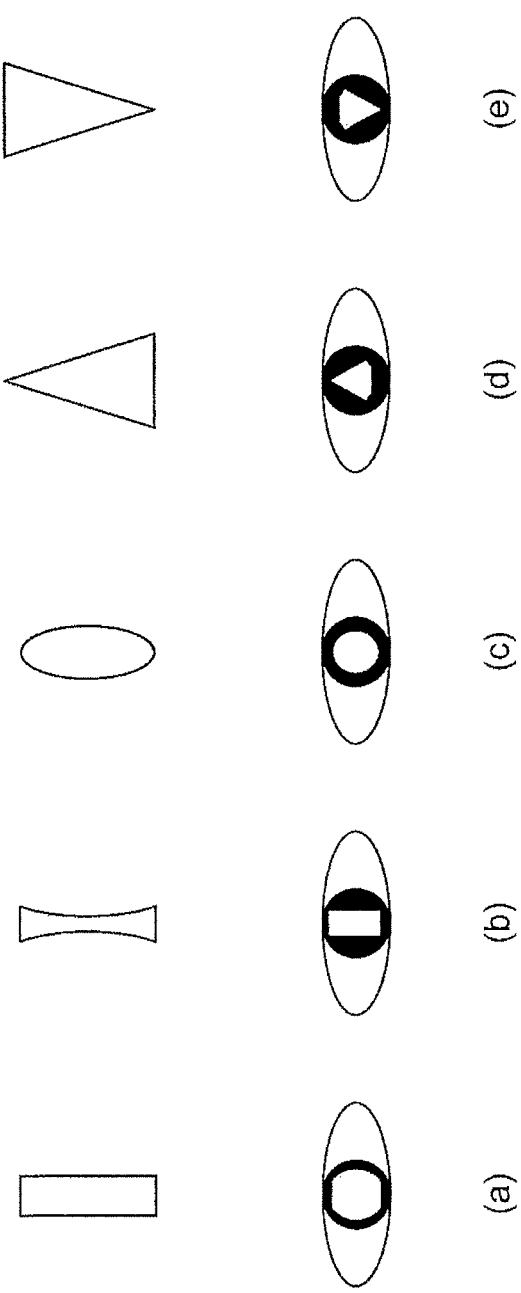
FIG. 12 includes views showing examples of the shape of a light emitting region 13 to be generated on the display section 3 of the tablet terminal 1A in FIG. 1.

Also, the light emitting region 13 to be generated on the display section 3 of the tablet terminal 1A can be changed to various shapes and sizes as long as the shape thereof is vertically long. The parts (a) to (e) in FIG. 12 show the shapes of light emitting regions in their upper parts, and in their lower parts, the shapes of reflection images on eye images obtained correspondingly thereto, respectively. Examples of the shape of the light emitting region 13 that can be mentioned include a rectangular shape as shown in the part (a) of FIG. 12, a band shape having a waist in the middle as shown in the part (b) of FIG. 12, an elliptical shape as shown in the part (c) of FIG. 12, and triangular shapes as shown in the parts (d) and (e) of FIG. 12. By forming such a triangular light emitting region, an eyelid position can be measured not only from the longitudinal length of a reflection image but also from the lateral width thereof, and a highly accurate measurement with the influence of a body motion, the apparatus position, and a gaze shift reduced is realized.

Figure 13:
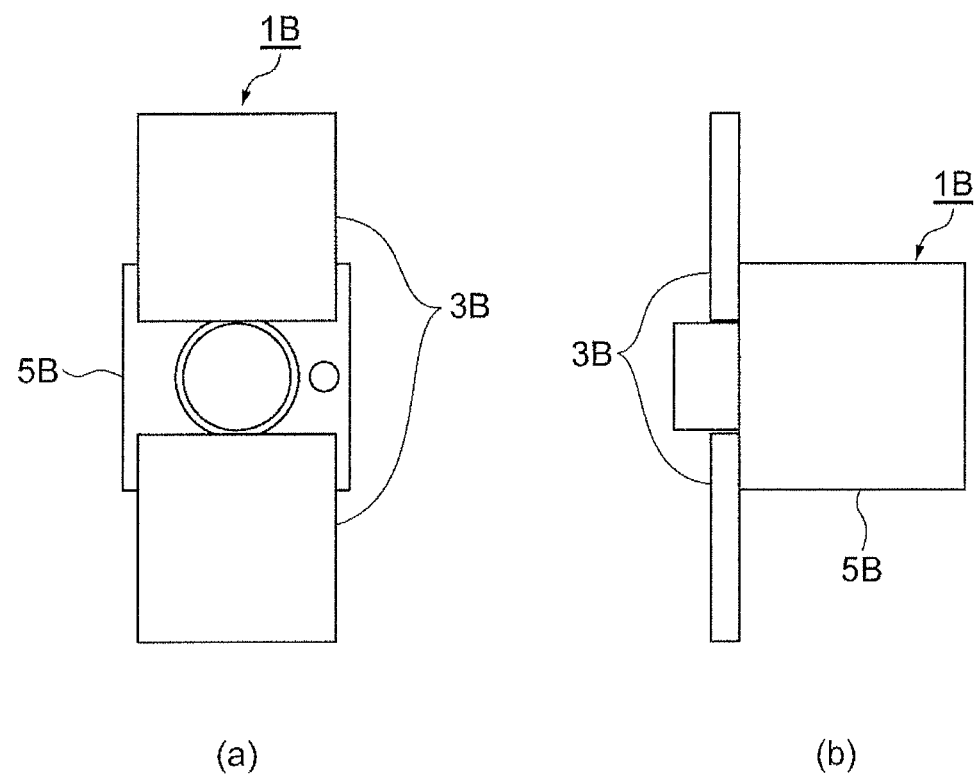
FIG. 13 includes views showing an external configuration of a measurement apparatus 1B according to a modification of the present invention.

Also, the present invention may be a dedicated apparatus for an eyelid position measurement such as a desktop type apparatus. FIG. 13 and FIG. 14 show external configurations of measurement apparatuses 1B and 1C according to modifications of the present invention, respectively, and each of the parts (a) and (b) of FIG. 13 and FIG. 14 is a front view, and a side view. The measurement apparatus 1B shown in FIG. 13 is constructed including a camera 5B such as a CMOS camera incorporated with an arithmetic section to process image data and surface light emitting sources 3B provided in a separate manner over and under an imaging lens of the camera 5B. The measurement apparatus 1C shown in FIG. 14 is an example for which the surface light emitting source 3B of the measurement apparatus 1B is replaced with a plurality of separated linear light emitting sources 3C. As in these measurement apparatuses 1B and 1C, the light emitting sources 3B, 3C can be variously adjusted in irradiation angle with respect to an imaging optical axis of the camera 5B, 5C so that an optimal reflection image can be obtained on the corneal surface. Also, the light emitting sources 3B, 3C have an emission wavelength set in the infrared region so as to have less influence on the subject.

Figure 15:
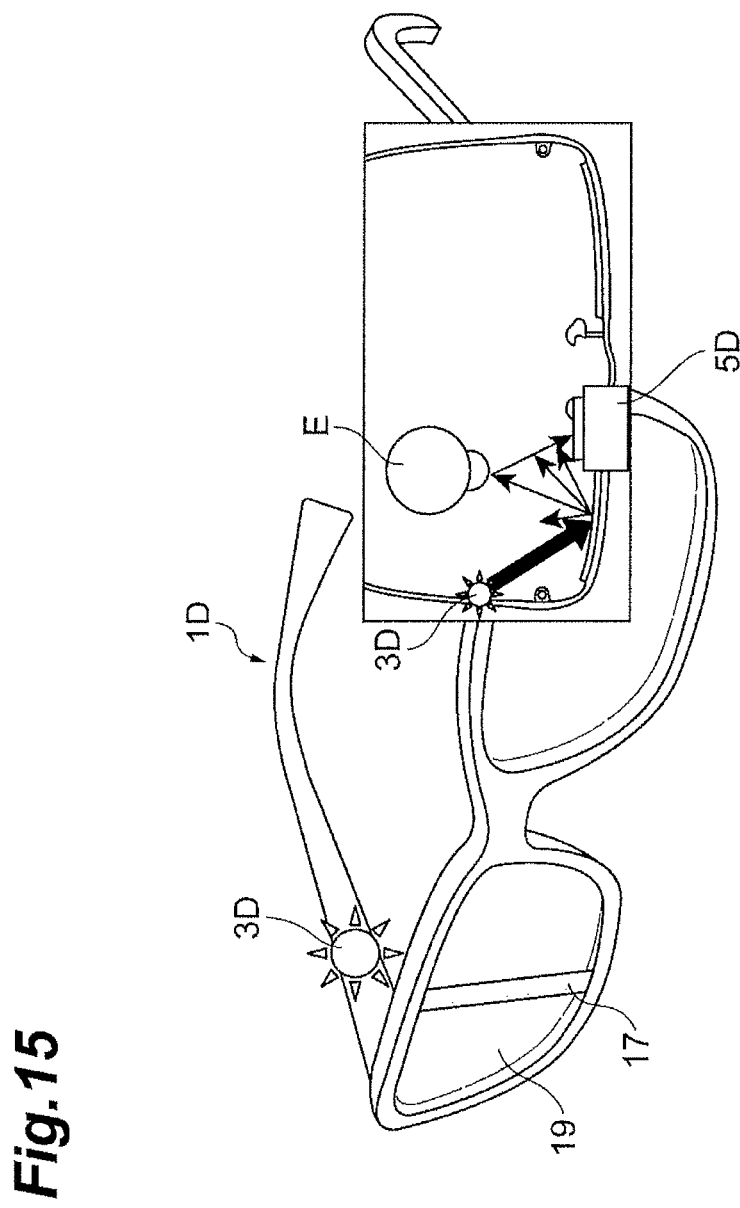
FIG. 15 is a view showing an external configuration of a measurement apparatus 1D according to a modification of the present invention.

Also, the present invention may be a spectacle type of measurement apparatus. FIG. 15 shows a configuration of a spectacle type measurement apparatus 1D according to a modification of the present invention. The spectacle type measurement apparatus 1D includes a light emitting section 3D provided in the part of a temple to irradiate illumination light such as infrared light toward the inside of an eyeglass 19, a scattering film 17 formed vertically long inside of the eyeglass 19 to form scattered light heading for a subject's eyeball E by scattering illumination light irradiated from the light emitting section 3D, and a camera 5D fixed in the vicinity of a bridge to obtain the subject's eye image. That is, the light emitting section 3D and the scattering film 17 in combination function as a light emitter that generates a vertically long light emitting region. In addition, the scattering film 17 may be changed to a groove that scatters illumination light from the light emitting section 3D, or in place of the light emitting section 3D and the scattering film 17, a spontaneous light emitter like an organic EL (Electro-Luminescence) element may be provided inside the eyeglass 19.

Also, in the embodiment described above, besides the light emitter for forming a reflection image for eyelid position detection, a light source such as an LED for generating a corneal reflection image may be separately provided. In this way, an upper end position of a reflection image can be relatively calculated using that corneal reflection image as a reference point in an eyelid position measurement processing. As a result, a highly accurate measurement with the influence of a body motion, the apparatus position, and a gaze shift reduced is realized.

Also, in the measurement apparatus of the embodiment described above, various types of sensors such as an acceleration sensor, a geomagnetic sensor, or a gyroscope sensor may be incorporated, and a measurement result of the eyelid position may be corrected based on a detection result of the sensor. For example, performing a separation analysis of the influence on the reflected light position of a body motion, apparatus inclination, or gaze shift during measurement using detection information such as an apparatus inclination obtained by the sensor and correcting errors due to the influence thereof allows improving measurement accuracy.

Here, in the above measurement apparatus, it is preferable that the arithmetic section derives at least one of the area, intensity, length, and length ratio of the reflection image as the reflection image information. In this manner, the rate of a part that is hidden by the eyelid of the reflection image on the conical surface is made evaluable, so that an eyelid position can be precisely measured by a simple evaluation method.

Also, it is preferable as well that the arithmetic section derives coordinates of a feature point of the reflection image as the reference image information. Also by such an arrangement of the arithmetic section, the rate of a part that is hidden by the eyelid of the reflection image on the corneal surface is made evaluable, so that an eyelid position can be precisely measured by a simple evaluation method.

It is preferable that the light emitter generates a band-like light emitting region. By adopting such an arrangement, an eyelid position can be precisely measured with a simple light emitter arrangement.

Also, it is preferable that an optical axis of the imaging section is set so as to be obliquely directed on the corneal surface with respect to an axis connecting the light emitter and the eyeball. In this manner, the reflection image on the corneal surface can be reliably captured by the imaging section.

Further, it is preferable that the above measurement apparatus is a terminal apparatus including the imaging section and a display device serving as the light emitter, and the display device functions as the light emitter by generating the light emitting region on a screen. By adopting such an arrangement, an eyelid position can be simply measured without adding a complex functional section to the terminal apparatus.

INDUSTRIAL APPLICABILITY

The present invention is used for application of a measurement apparatus and a measurement method for measuring a subject's eyelid position, and enables more precisely measuring the subject's eyelid position.

REFERENCE SIGNS LIST

1 . . . subject; 1A . . . tablet terminal (measurement apparatus); 1B, 1C, 1D . . . measurement apparatus; 3 . . . display section (light emitter); 3B, 3C . . . light emitting source (light emitter); 3D . . . light emitting section (light emitter); 5, 5B, 5C, 5D . . . camera (imaging section); 7 . . . arithmetic circuit (arithmetic section); 13 . . . light emitting region; 17 . . . scattering film (light emitter); E . . . eyeball; L1 . . . imaging optical axis; L2 . . . axis; S . . . subject; Ta . . . upper eyelid.

The invention claimed is:
1. A measurement apparatus for measuring a subject's eyelid position, comprising:
 a terminal apparatus including
  a display device having a screen disposed in the center of a surface of the terminal apparatus, the screen configured to generate a vertically elongated light emitting region on a part of the screen to make a reflection image form on a corneal surface of the subject's eyeball, and
  an imaging device disposed outside of the screen on the surface of the terminal apparatus, the imaging device configured to image the reflection image formed by the display device; and
 an arithmetic circuit configured to derive reflection image information concerning a size or position of the reflection image based on image data of the reflection image obtained by the imaging device, and measure the eyelid position based on the reflection image information,
 wherein the imaging device includes an image sensor and an optical element for forming an image on the image sensor,
 wherein an optical axis of the image sensor is directed outside an axis extending perpendicularly from the surface of the terminal apparatus,
 wherein the screen is configured to generate the vertically elongated light emitting region on the part of the screen by brightening the part of the screen, and
 wherein the arithmetic circuit derives barycentric coordinates of the reflection image as the reflection image information.

2. The measurement apparatus according to claim 1, wherein
the arithmetic circuit derives at least one of an area, intensity, length, and length ratio of the reflection image as the reflection image information.

3. The measurement apparatus according to claim 1, wherein
the arithmetic circuit derives coordinates of a feature point of the reflection image as the reflection image information.

4. The measurement apparatus according to claim 1, wherein
the display device generates a band shaped light emitting region.

5. The measurement apparatus according to claim 1, wherein
an optical axis of the imaging device is set so as to be obliquely directed on the corneal surface with respect to an axis connecting the display device and the eyeball.

6. The measurement apparatus according to claim 1, wherein
the display device is configured to display an image on the screen based on an image data, and generate an image of the vertically elongated light emitting region on the screen.

7. A measurement method for measuring a subject's eyelid position, comprising:
making a reflection image form on a corneal surface of the subject's eyeball using a display device having a screen and that generates a vertically elongated light emitting region on a part of the screen by brightening the part of the screen, the screen being disposed in the center of a surface of a terminal apparatus;
imaging the reflection image formed on the corneal surface of the subject's eyeball using an imaging device disposed outside of the screen on the surface of the terminal apparatus, the imaging device including an image sensor and an optical element for forming an image on the image sensor, wherein an optical axis of the image sensor is directed outside an axis extending perpendicularly from the surface of the terminal apparatus; and
deriving reflection image information concerning a size or position of the reflection image based on image data of the reflection image obtained by the imaging of the reflection image, and measuring the eyelid position based on the reflection image information,
wherein the reflection image information includes barycentric coordinates of the reflection image.

8. The measurement method according to claim 7, wherein
deriving the reflection image information includes deriving at least one of an area, intensity, length, and length ratio of the reflection image.

9. The measurement method according to claim 7, wherein
deriving the reflection image information includes deriving coordinates of a feature point of the reflection image.

10. The measurement method according to claim 7, wherein
the display device generates a band shaped light emitting region.

11. The measurement method according to claim 7, wherein
imaging the reflection image includes setting an optical axis of the imaging device so as to be obliquely directed on the corneal surface with respect to an axis connecting the display device and the eyeball.

12. The measurement method according to claim 7, wherein
the display device is configured to display an image on the screen based on an image data, and generate an image of the vertically elongated light emitting region on the screen.

* * * * *